United States Patent
Kim et al.

(10) Patent No.: US 9,551,004 B2
(45) Date of Patent: Jan. 24, 2017

(54) TRANSGENIC TREE INDUCED BY RABG3BCA AND USE THEREOF

(75) Inventors: Ohk Mae Kim, Seoul (KR); Soon Il Kwon, Gunpo-si (KR); Hong Joo Cho, Seoul (KR); Eun Woon Noh, Suwon-si (KR); Kyoung Heon Kim, Seoul (KR); Young Hoon Jung, Gwangju (KR)

(73) Assignee: KOREA UNIVERSITY RESEARCH AND BUSINESS FOUNDATION (KR)

( * ) Notice: Subject to any disclaimer, the term of this patent is extended or adjusted under 35 U.S.C. 154(b) by 110 days.

(21) Appl. No.: 14/241,278

(22) PCT Filed: Aug. 29, 2012

(86) PCT No.: PCT/KR2012/006876
§ 371 (c)(1),
(2), (4) Date: Feb. 26, 2014

(87) PCT Pub. No.: WO2013/032212
PCT Pub. Date: Mar. 7, 2013

(65) Prior Publication Data
US 2015/0299719 A1 Oct. 22, 2015

(30) Foreign Application Priority Data

Aug. 30, 2011 (KR) .................. 10-2011-0087129
Aug. 28, 2012 (KR) .................. 10-2012-0094285

(51) Int. Cl.
*C12N 15/82* (2006.01)
*C12P 19/02* (2006.01)
*C12P 19/14* (2006.01)
*C07K 14/415* (2006.01)

(52) U.S. Cl.
CPC ......... *C12N 15/8246* (2013.01); *C07K 14/415* (2013.01); *C12N 15/8243* (2013.01); *C12N 15/8255* (2013.01); *C12N 15/8261* (2013.01); *C12P 19/14* (2013.01); *C12P 19/02* (2013.01); *Y02E 50/16* (2013.01)

(58) Field of Classification Search
None
See application file for complete search history.

(56) References Cited

U.S. PATENT DOCUMENTS 7,723,110 B2 * 5/2010 Chang ................ C12N 15/8261
435/320.1

FOREIGN PATENT DOCUMENTS

JP        2010-233536 A     10/2010
WO      WO-9403646 A1     2/1994

OTHER PUBLICATIONS

Kwon et al, Plant Journal (2010) 64: 151-164.*
Kwon et al (2009 J. Plant Biol. 52:79-87).*
Kwon, Soon Il et al., "Overexpression of constitutively active Arabidopsis RabG3b promotes xylem development in transgenic poplars," Plant, Cell and Environment, vol. 34:2212-2224 (2011).
Abramson et al. "Plant Cell Wall Reconstruction Toward Improved Lignocellulosic Production and Processability." *Plant Sci.* 178(2010):61-72.
Baucher et al. "Lignin: Genetic Engineering and Impact on Pulping." *Crit. Rev. Biochem. Mol. Biol.* 38(2003):305-350.
Chaffey et al. "Understanding the Role of the Cytoskeleton in Wood Formation in Angiosperm Trees: Hybrid Aspent (*Populus tremula* x *P. tremuloides*) as the Model Species." *Tree Physiol.* 22(2002):239-249.
Chen et al. "Lignin Modification Improves Fermentable Sugar Yields for Biofuel Production." *Nat. Biotechnol.* 25.7(2007):759-761.
Choi et al. "An Efficient and Novel Plant Selectable Marker Based on Organomercurial Resistance." *J. Plant Biol.* 48.4(2005):351-355.
Chomczynski et al. "DNAzol®: A Reagent for the Rapid Isolation of Genomic DNA." *BioTechniques.* 22(1997):550-553.
Courtois-Moreau et al. "A Unique Program for Cell Death in Xylem Fibers of *Populus* Stem." *Plant J.* 58(2009):260-274.
Déjardin et al. "Wood Formation in Angiosperms." *C. R. Biologies.* 333(2010):325-334.
Demura et al. "Regulation of Plant Biomass Production." *Curr. Opin. Plant Biol.* 13(2010):299-304.
Dinus. "Genetic Improvement of Poplar Feedstock Quality for Ethanol Production." *Appl. Biochem. Biotechnol.* 91(2001):23-34.
Du et al. "The *Populus* Homeobox Gene ARBORKNOX2 Regulates Cell Differentiation During Secondary Growth." *Plant J.* 60(2009):1000-1014.
Fillatti et al. "*Agrobacterium* Mediated Transformation and Regeneration of *Populus.*" *Mol. Gen. Genet.* 206(1987):192-199.
Fukuda. "Programmed Cell Death of Tracheary Elements as a Paradigm in Plants." *Plant Mol. Biol.* 44(2000):245-253.
Kamm et al. "Principles of Biorefineries." *Appl. Microbiol. Biotechnol.* 64(2004):137-145.
Kaneda et al. "Secondary Cell Wall Deposition in Developing Secondary Xylem of Poplar." *J. Integr. Plant Biol.* 52.2(2010):234-243.
Kim et al. "Transgenic Poplar Expressing *Arabidopsis* NDPK2 Enhances Growth as Well as Oxidative Stress Tolerance." *Plant Biotechnol. J.* 9(2011):334-347.
Kwon et al. "Role of an *Arabidopsis* Rab GTPase RabG3b in Pathogen Response and Leaf Sequence." *J. Plant Biol.* 52(2009):79-87.
Kwon et al. "Role of Arabidopsis RabG3b and Autophagy in Tracheary Element Differentiation." *Autophagy.* 6(2010):1187-1189.

(Continued)

*Primary Examiner* — Brent Page
(74) *Attorney, Agent, or Firm* — Mintz Levin Cohn Ferris Glovsky and Popeo, P.C.; Fred C. Hernandez; Linyu L. Mitra

(57) ABSTRACT

Provided to a transgenic tree induced by RabG3bCA and a use thereof. The transgenic tree serves to control xylem growth through RabG3b of *Arabidopsis thaliana*, and this function is involved in the growth of poplars. Particularly, the transgenic tree is valuable for industrial use since the increase in length of a fiber cell, which is the most important factor of determining pulp quality, is confirmed.

7 Claims, 10 Drawing Sheets

(56) References Cited

OTHER PUBLICATIONS

Kwon et al. "The Rab GTPase RabG3b Functions in Autophagy and Contributes to Tracheary Element Differentiation in Arabidopsis." *Plant J.* 64(2010):151-164.
Lynd et al. "Biocommodity Engineering." *Biotechnol. Prog.* 15(1999):777-793.
Okumura et al. "Transformation of Poplar (*Populus alba*) Plastids and Expression of Foreign Proteins in Tree Chloroplasts." *Transgenic Res.* 15(2006):637-646.
Pauly et al. "Plant Cell Wall Polymers as Precursors for Biofuels." *Curr. Opin. Plant Biol.* 13(2010):305-312.
Pilate et al. "Field and Pulping Performances of Transgenic Trees with Altered Lignification." *Nat. Biotechnol.* 20(2002):607-612.
Sannigrahi et al. "Polar as a Feedstock for Biofuels: A Review of Compositional Characteristics." *Biofuels, Bioprod., Bioref.* 4(2010):209-226.
Schmittgen et al. "Analyzing Real-Time PCR Data by the Comparative CT Method." *Nat. Protoc.* 3.6(2008):1101-1108.
Segal et al. "An Empirical Method for Estimating the Degree of Crystallinity of Native Cellulose Using the X-Ray Diffractometer." *Textile Res. J.* 29(1959):786-794.
Selig et al. "Enzymatic Saccharification of Lignocellulosic Biomass." National Renewable Energy Laboratory, Technical Report: NREL/TP-510-42629. (Mar. 2008).
Service. "Biofuel Researchers Prepare to Reap a New Harvest." *Science.* 315.5818(2007):1488-1491.
Shi et al. "Towards a Systems Approach for Lignin Biosynthesis in *Populus trichocarpa*: Transcript Abundance and Specificity of the Monolignol Biosynthetic Genes." *Plant Cell Physiol.* 51.1(2010):144-163.
Shin et al. "Conversion Factors for Carbohydrate Analysis by Hydrolysis and 1 H-NMR Spectroscopy." *Cellulose.* 15(2008):255-260.
Sluiter et al. "Determination of Structural Carbohydrates and Lignin in Biomass." National Renewable Energy Laboratory, Technical Report: NREL/TP-510-42618. (Jul. 2011).
Song et al. "Characterization of Cellulose Synthase Complexes in *Populus* Xylem Differentiation." *New Phytologist.* 187(2010):777-790.
Sticklen. "Plant Genetic Engineering to Improve Biomass Characteristics for Biofuels." *Curr. Opin. Biotechnol.* 17(2006):315-319.
Tuskan et al. "The Genome of Black Cottonwood, *Populus trichocarpa* (Torr. & Gray)." *Science.* 313(2006):1596-1604.
Via et al. "Effects of Cytokines on Mycobacterial Phagosome Maturation." *J. Cell Sci.* 111(1998):897-905.
Weir et al. "Flow Cytometric Analysis of Tracheary Element Differentiation in *Zinnia elegans* Cells." *Cytomet Part A.* 68A(2005):81-91.
Weng et al. "Emerging Strategies of Lignin Engineering and Degradation for Cellulosic Biofuel Production." *Curr. Opin. Biotechnol.* 19(2008):166-172.
Yang et al. "Effect of Xylan and Lignin Removal by Batch and Flowthrough Pretreatment on the Enzymatic Digestibility of Corn Stover Cellulose." *Biotechnol. Bioeng.* 86.1(2004):88-95.

\* cited by examiner (a)

(b)

(a)

(b)

SEQUENCE LISTING

```
<160> NUMBER OF SEQ ID NOS: 49

<210> SEQ ID NO 1
<211> LENGTH: 609
<212> TYPE: DNA
<213> ORGANISM: Artificial Sequence
<220> FEATURE:
<223> OTHER INFORMATION: Chemically Synthesized

<400> SEQUENCE: 1
atgtcgacgc gaagacgaac tttactcaaa gttataattc ttggagacag cggggttggc      60
aaaacatcgt tgatgaatca atatgtgaat aacaagttta gtcaacagta caaagctacg     120
atcggagctg attttgtcac taaggagctt caaattgatg acaggcttgt cacattgcaa     180
atatgggaca ctgctgggct agagaggttt caaagtcttg gtgttgcttt ctatagaggt     240
gcagattgtt gtgttcttgt ctatgatgtg aatcacttga agtcatttga atctctcgac     300
aattggcaca acgagtttct tacacgggct agtccacgtg acccaatggc attccctttt     360
atacttcttg gtaataaggt tgatattgat ggaggaaata gccgagtggt atctgagaag     420
aaggctagag aatggtgtgc tgaaaaggga aacatagtct atttcgagac atcggctaaa     480
gaagattaca atgtcgatga ctccttcttg tgcatcacaa aacttgccct tgcaaatgaa     540
cgcgaccaag atatatattt ccagccagat actggttcgg tgcctgagca aagaggaggt     600
tgtgcttgc                                                             609

<210> SEQ ID NO 2
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 2
```
atgacaggct tgtcacattg ca                                    22

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
agcacaacct cctctttgct ca                                    22

<210> SEQ ID NO 4
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 4
cattggtgct gagcgattcc gttgc                                 25

<210> SEQ ID NO 5
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 5
ttttcatgct gcttggggct agtgc                                 25

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 6
actagcccat ccagagatat ccga                                  24

<210> SEQ ID NO 7
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 7
tcatcttcgg tggcctgaga cttt                                  24

<210> SEQ ID NO 8
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 8
gtatgacctt agtgaagaca caatcat                               27

<210> SEQ ID NO 9
<211> LENGTH: 23
<212> TYPE: DNA

```
<213> ORGANISM: Artificial Sequence
<220> FEATURE:
<223> OTHER INFORMATION: Chemically Synthesized

<400> SEQUENCE: 9
cccttgggtt cttgattagc ctc                                              23

<210> SEQ ID NO 10
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 10
cagtaattca gaaagctggt gttgc                                            25

<210> SEQ ID NO 11
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 11
gcatccacaa agatgaaatc aaaac                                            25

<210> SEQ ID NO 12
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 12
tcttgaagaa ttgctatgac gcct                                             24

<210> SEQ ID NO 13
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 13
gaatgcactc aacaagtatc accttg                                           26

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 14
ggcaagctga tcttgatggg tgtt                                             24

<210> SEQ ID NO 15
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 15
tcccggtgat tgactttctc ccaa                                             24
```

<210> SEQ ID NO 16
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 16
tgaccgtctg tctttgcttt taaa                                    24

<210> SEQ ID NO 17
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 17
gggacagatc accagatgca                                         20

<210> SEQ ID NO 18
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 18
tcccatgttc tcgaaccctt ta                                      22

<210> SEQ ID NO 19
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 19
ccagggtatt gccgatgtta ag                                      22

<210> SEQ ID NO 20
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 20
gagttaagga agatggagag gtgt                                    24

<210> SEQ ID NO 21
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 21
tgcactgagg acaggactgg ttgc                                    24

<210> SEQ ID NO 22
<211> LENGTH: 24
<212> TYPE: DNA
<213> ORGANISM: Artificial Sequence
<220> FEATURE:

<223> OTHER INFORMATION: Chemically Synthesized

<400> SEQUENCE: 22
tcgcctttct ctcagatacg aacg                                    24

<210> SEQ ID NO 23
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 23
ttacccgtaa caagaggggg ttcc                                    24

<210> SEQ ID NO 24
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 24
gttggcctct gtcttctctc ttgtc                                   25

<210> SEQ ID NO 25
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 25
caatctatag aaatgcaggt ttcac                                   25

<210> SEQ ID NO 26
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 26
gttggcctct gtcttctctc ttgtt                                   25

<210> SEQ ID NO 27
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 27
caatcaatgg aaatgcaggt ctccg                                   25

<210> SEQ ID NO 28
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 28
gaaaatttca agcccaacga                                         20

```
<210> SEQ ID NO 29
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 29
ctggaggcag tgttcctagc                                                 20

<210> SEQ ID NO 30
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 30
ggctgagtgg gattgttcat                                                 20

<210> SEQ ID NO 31
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 31
aggcctttta tccgtttcgt                                                 20

<210> SEQ ID NO 32
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 32
acgtttgacc catacgaagc                                                 20

<210> SEQ ID NO 33
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 33
cgtgagaggc aacaaagaca                                                 20

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 34
gctagccatg aaggaagtgc                                                 20

<210> SEQ ID NO 35
<211> LENGTH: 20
<212> TYPE: DNA
<213> ORGANISM: Artificial Sequence
<220> FEATURE:
<223> OTHER INFORMATION: Chemically Synthesized
```

```
<400> SEQUENCE: 35
ggaatccatg ttccatgtcc                                          20

<210> SEQ ID NO 36
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 36
tttgctgagg caattgtgag                                          20

<210> SEQ ID NO 37
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 37
gcctctcacg ctttgatttc                                          20

<210> SEQ ID NO 38
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 38
tcgcagtatg ggatgaaaca                                          20

<210> SEQ ID NO 39
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 39
gcttcaatta ggcgctgaac                                          20

<210> SEQ ID NO 40
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 40
cagccacgag ttcttcatca                                          20

<210> SEQ ID NO 41
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 41
agacaaactg ccccacagtc                                          20

<210> SEQ ID NO 42
<211> LENGTH: 20
```

```
<212> TYPE: DNA
<213> ORGANISM: Artificial Sequence
<220> FEATURE:
<223> OTHER INFORMATION: Chemically Synthesized

<400> SEQUENCE: 42
actccaaacg tctcccttt                                           20

<210> SEQ ID NO 43
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 43
catgctcttg cttgaagctg                                          20

<210> SEQ ID NO 44
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 44
agcaaaggct ggaagaatca                                          20

<210> SEQ ID NO 45
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 45
tgaatgaatt gcccaacaga                                          20

<210> SEQ ID NO 46
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 46
ggcaaggaga aggtacacat                                          20

<210> SEQ ID NO 47
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 47
caatcacacg cttgtcaata                                          20

<210> SEQ ID NO 48
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 48
```

```
tcaactttcg atggtaggat agtg                                                24

<210> SEQ ID NO 49
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 49
ccgtgtcagg attgggtaat tt                                                  22
```

TRANSGENIC TREE INDUCED BY RABG3BCA AND USE THEREOF

CROSS-REFERENCE TO RELATED APPLICATION

This application is a national stage application, filed under 35 U.S.C. §371, of International Application No. PCT/KR2012/006876, filed Aug. 29, 2012, which claims priority to and the benefit of Korean Patent Application No. 2011-0087129, filed Aug. 30, 2011, Korean Patent Application No. 2012-0094285, filed Aug. 28, 2012, the contents of which are incorporated herein by reference in their entireties.

SEQUENCE LISTING

The instant application contains a Sequence Listing which has been submitted via EFS-Web. The contents of the text file named "46278-510N01US_ST25.txt", which was created on May 1, 2015, and is 10,610 bytes in size, are hereby incorporated by reference in their entirety.

TECHNICAL FIELD

The present invention relates to a transgenic tree induced by RabG3bCA (hereinafter, referred to as a "RabG3bCA transgenic tree") and a use thereof.

BACKGROUND ART

It is reported that carbon-based plants present in the Earth reach 10 times of the world oil consumption and 5 times of all kinds of energy consumption. Biomass products used in the world are sequentially rice straw, wheat straw, corn stover, and bagasse, and the total amount of the biomass products is 1,549 trillion kg. Recently, to stably produce plant bio energy attracting attention as the next generation environmentally friendly energy source capable of replacing fossil fuel, attention to development of biomass plants having high productivity is increasing. Raw materials of alternative energy bioethanol which now become the biggest issue are roughly classified into saccharides (sugar cane, sugar beet, etc.), starches (corn, potato, sweet potato, etc.), and lignocelluloses (lumber from thinning, waste wood, rice straw, etc.). All of commercialized bioethanol-producing techniques use food resources such as saccharide-based and starch-based biomasses as raw materials, and have a very close relationship with food supply for humans. A technique using a lignocellulosic biomass called the second generation biomass that is cheaper and has a less problem in supply of raw materials is actively being developed to overcome the above-described problems in the long term. As representative lignocellulosic biomass plants, poplars and eucalyptuses are used, and woods of these trees have attracted attention as an important material for producing various products such as papers, pulps, or fibers, and bioethanol. Due to such economic importance, studies for increasing the quantity and quality of woods are progressing, and thus a study for a synthesis pathway and a mechanism of controlling synthesis of woods is very important. A wood layer of a tree is composed of a secondary xylem, which is usually composed of a vessel element and fibers. In the angiosperm such as a poplar or eucalyptus, wood, that is, the secondary xylem, is formed in a vascular cambium, and completed through formation of a secondary cell wall and development of programmed cell death. Recently, the poplar is a model tree for study, and becomes an important plant for study as a tree for a biomass. Particularly, construction of various molecular biological databases and system establishment including decoding of gene sequence of the poplar, EST, microarray data accumulation, development of a molecular marker, and establishment of transforming technology become important bases for activating studies on poplars.

To develop the tree for a biomass, quantitative and qualitative increases in wood, that is, a xylem should be carried out. To this end, based on the understanding of a molecular mechanism of xylem development, it is essential to study the formation of a secondary cell wall and a process of the programmed cell death. The study on the formation of the secondary cell wall is very actively progressing, but relatively, the study on the programmed cell death is insignificant. Phenomenologically, the process of the programmed cell death sequentially includes vacuole collapse, secretion and activation of various lyases, and degradation of a cytoplasm, and thus formation of a xylem is observed. However, specific molecular mechanisms or critical regulatory factors are not mostly known. In the laboratory, autophagy is considered to be an important process to control the programmed cell death, and for the past several years, studies on the autophagy and the programmed cell death mechanism have been performed. Meanwhile, in the year of 2000, according to Fukuda Laboratory, probability of relating autography during the programmed cell death to differentiation of a vessel element has been disclosed, but there was no subsequent study thereon. To define a mechanism of xylem development derived from a vascular cambium, particularly, in addition to a molecular-level study on vessel element differentiation, during the vessel element differentiation, studies on the function of the autophagy and interrelation between the programmed cell death and the autophagy should be essentially performed. Accordingly, as the xylem development is stimulated and the qualitative and quantitative increases of wood layers are induced, development of lignocelluloses biomass plants ultimately useful in the industry can be successfully carried out.

To establish a "sugar platform" including various liquid fuels such as ethanol and butanol or value-added products in various ranges including a monomer of a raw polymer such as polylactic acid produced from fermentative sugar such as glucose, lignocellulose-derived biorefineries such as crude oil refineries now receive attention as a promising industry [Kamm, B., Kamm, M. 2004. Principles of biorefineries. *Appl Microbiol Biotechnol,* 64(2), 191 137-45; Lynd, L. R., Wyman, C. E., Gerngross, T. U. 1999. Biocommodity Engineering. *Biotechnol* 198 *Prog,* 15(5), 777-93]. Development of materials offering high cost efficiency is one of the main challenges for industrialization, and various studies relating to the development of an exclusive lignocellulose biomass are still progressing in the world including the U.S. and Europe. Due to a high growth rate and short-term circulation, the poplar is a representative biomass product in the art [Sannigrahi, P., Tuskan, G. A., Ragauskas, A. J. 2010. Poplar as a feedstock for biofuels: a 200 review of compositional characteristics. *Biofuels Bioprod Bioref,* 4, 209-226]. In addition, such a perennial tree is enriched with the main components for sugar turnover (conversion), which are cellulose and hemicelluloses, and does not need an input of large amounts of chemical products, and thus smaller investment in cultivation is needed [Baucher, M., Halpin, C., Petit-Conil, M., Boerjan, W. 2003. Lignin: genetic engineering and 166 impact on pulping. *Crit Rev Biochem Mol Biol,* 38(4), 305-50]. Until now, since the conversion into a lignocellulose is dependent on a specific gravity of wood and contents of lignin and cellulose, some studies relating to genetic engineering modifications have been performed. Details relating to genetic engineering improvement of poplars can be confirmed from the following literatures [Chen, F., Dixon, R. A. 2007. Lignin modification improves fermentable sugar yields for 168 biofuel production. *Nat Biotechnol*, 25(7), 759-61; Dinus, R. J. 2001a. Genetic improvement of poplar feedstock quality for ethanol production. 170 *Appl Biochem Biotechnol*, 91-93, 23-34; Sannigrahi, P., Tuskan, G. A., Ragauskas, A. J. 2010. Poplar as a feedstock for biofuels: a 200 review of compositional characteristics. *Biofuels Bioprod Bioref*, 4, 209-226]. In fact, the improvement of poplars through genetic modifications caused by 50% reduction of lignin was reported in 1999 [Service, R. F. 2007. Cellulosic ethanol. Biofuel researchers prepare to reap a new harvest. 204 *Science*, 315(5818), 1488-91]. However, until now, there is no study practically showing a systematic approach for utilizing genetically-modified plants including poplars to produce sugar.

The present inventors perform a study on differentiation of a vessel element as a representative cell layer of a xylem. Particularly, a small GTP-binding protein, RabG3b, which is found by analysis of secretive protein of *Arabidopsis thaliana*, is concerned, involved in the autophagy and vessel element differentiation, and probability of involving the autophagy in the vessel element differentiation is considered. Through various molecular-biological and cellular studies, it is known that the RabG3b is involved in vessel element differentiation in plants, that is, the xylem development, which is a mechanism performed by a function of the RabG3b to control the autophagy. Moreover, it is defined that the autophagy is an important process in the vessel element differentiation. When RabG3bCA is overexpressed in *Arabidopsis thaliana*, it is seen that both of length growth and thickness growth are increased compared to those of a wild-type plant, and it is confirmed that such growths are stimulated by the xylem development [Korean Patent Application No. 2010-0085609].

DISCLOSURE

Technical Problem

Specific genetic characters of most plants are found. However, when the characters are applied to heterogeneous plants, the plants do not exhibit the same effect in general. Particularly, it is common that genetic characters of herbaceous plants are not shown in tree plants. However, the present inventors developed a tree having the same character (xylem development) as that in *Arabidopsis thaliana* by overexpressing a mutant RabG3bCA, which is the active form of RabG3b derived from *Arabidopsis thaliana*. In addition, change in composition of an RabG3bCA transgenic tree developed in the present invention was analyzed. The tree was pre-treated with a specific catalyst, and hydrolyzed by adding an enzyme, such as a cellulase, at a suitable amount. Subsequently, a probability of a transgenic tree was confirmed in an economic aspect by establishing material balances throughout an entire process. Compared to a wild-type tree, the RabG3bCA transgenic tree of the present invention is expected to be very useful in an industrial aspect since paper or pulp is produced by the increase in length of a fiber cell, and bioethanol can be produced by the increase in contents of cellulose and/or glucose.

Accordingly, the present invention is directed to providing a transgenic tree induced by a mutant gene, RabG3bCA, which is the active form of RabG3b derived from *Arabidopsis thaliana*.

The present invention is also directed to providing a paper made from an RabG3bCA transgenic tree and a pulp produced from the transgenic tree.

The present invention is also directed to providing a biomass produced from an RabG3bCA transgenic tree.

The present invention is also directed to providing a method of producing a biomass using an RabG3bCA transgenic tree.

Technical Solution

The present invention provides a tree transformed by a mutant RabG3bCA, which is the active form of RabG3b.

The present invention provides a paper made from an RabG3bCA transgenic tree and a pulp produced from the transgenic tree.

The present invention provides a biomass produced from an RabG3bCA transgenic tree.

The present invention provides a method of producing a biomass using an RabG3bCA transgenic tree.

Advantageous Effects

An RabG3bCA transgenic tree was manufactured and subjected to primary character analysis, thereby observing biomass-related characteristics. That is, the transgenic tree is increased in length and thickness growth, and particularly, a xylem, that is, a wood layer is increased by 40% or more. In addition, the result that the most important factor of determining the quality of a paper or pulp, the length of a fiber cell, was increased by 50% or more is obtained.

In addition, as the result of analysis of chemical components, while a content of cellulose and/or glucose, which becomes a raw material of a bioethanol, is increased by about 10%, a content of hemicellulose interrupting degradation of cellulose is decreased by 25%. Accordingly, it is seen that the RabG3bCA transgenic tree according to the present invention can be useful as a tree for biomass/bioenergy, which has an industrial value.

MODES OF INVENTION

Figure 1:
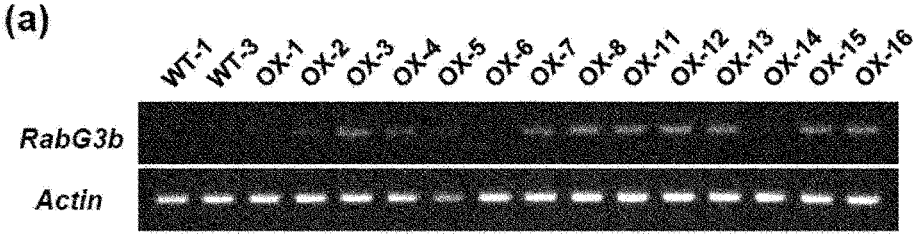
FIG. 1 shows results obtained by comparing expression of RabG3b between a wild-type tree (WT) and a transgenic poplar (OX) [(a) semi-quantitative real-time PCR analysis for RabG3bCA expression, actin was used as a control; and (b) analysis of RabG3b expression by western blotting, extracted from leaves at the $4^{th}$ internode (between two nodes) of stems, and Ponceau S staining was shown as a loading control].
Figure 1:
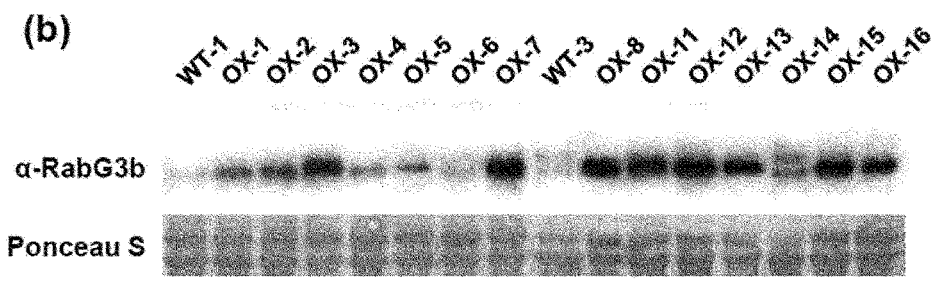

The present invention relates to a transgenic tree induced by a mutant gene (RabG3bCA), which is the active form of RabG3b.

The tree may refer to every kinds of trees becoming a raw material for paper or pulp, including, broadleaf trees such as an eucalyptus, birch, beech, poplar, cotton wood and oak, and needleleaf trees such as a pine, fir, and larch.

In the present invention, RabG3b is derived from *Arabidopsis thaliana* (*Arabidopsis*), but an RabG3b gene or an analog thereof derived from a different species of a target may also be used.

The RabG3bCA gene is represented as a base sequence of SEQ. ID. NO. 1.

In the transgenic tree according to the present invention, the amount(s) of cellulose and/or glucose is(are) higher than that of the wild-type plants. In addition, the length of a fiber cell is increased. These are the results obtained from a xylem-increased character.

In addition, the present invention may include a pulp produced from the transgenic tree or a paper made from the transgenic tree.

In addition, the present invention may include a biomass produced from the transgenic tree.

In addition, the present invention may include a method of producing a biomass using the transgenic tree. The method of the present invention is performed in the same manner as a general method of producing a biomass using wood. The biomass may include all kinds of biomasses produced from lignocelluloses, and specifically, saccharides such as cellulose, glucose, etc. Particularly, the present invention may also include pre-treating the transgenic tree with sodium hydroxide, and hydrolyzing the pre-treated tree with an enzyme to produce a biomass.

In addition, the present invention may include a method of producing a pulp using the transgenic tree. The method of the present invention is performed in the same manner as a general method of producing a pulp using wood.

In addition, the present invention includes a method of manufacturing a transgenic tree having increased cellulose and/or glucose by overexpressing a mutant gene (RabG3bCA), which is the active form of RabG3b.

Hereinafter, detailed description on transgenic poplars according to an exemplary embodiment of the present invention is as follows.

A poplar has environmental and economical values, and is important in the wood industry [Kaneda et al. (2010) Journal of Integrative Plant Biology 52, 234-243]. The most important biological resource of a tree is a tree or a secondary xylem part, which is used to produce a recyclable paper, pulp, or biomass [Demura et al. (2010) Current Opinion in Plant Biology 13, 299-304]. Recently, genetic and genetic engineering studies have revealed several important genes used in the process of producing a tree, and widened the understanding to the process of producing a tree. However, the present inventors showed that the RabG3bCA has a relationship with a catalytic action of xylem development in *Arabidopsis thaliana* from the results of the previous invention, and the RabG3bCA is increased in poplars, thereby changing a tree-producing ability according to the present invention. That is, in RabG3bCA-overexpressed poplars, a growth rate of stems and xylem development are increased. Such effects are conserved between *Arabidopsis thaliana* and poplars, and thus it is shown that the RabG3bCA of *Arabidopsis thaliana* is also functionally homologous in the poplars. Referring to the results of analysis of the poplar genome (JGI Genome Portal homepage; Tuskan et al. 2006), 8 poplar homologs exhibit approximately 70% similarity to the amino acid sequence of the RabG3b of *Arabidopsis thaliana*, and one (estExt_Genewise1_v1.C_LG_II2093) of the homologs has a high similarity (90%) and identity (83%) with respect to the RabG3b protein of *Arabidopsis thaliana*. It will be worthwhile to know whether these RabG3b homologs are functionally similar to the RabG3b of *Arabidopsis thaliana* and have the influence on xylem development.

Figure 7:
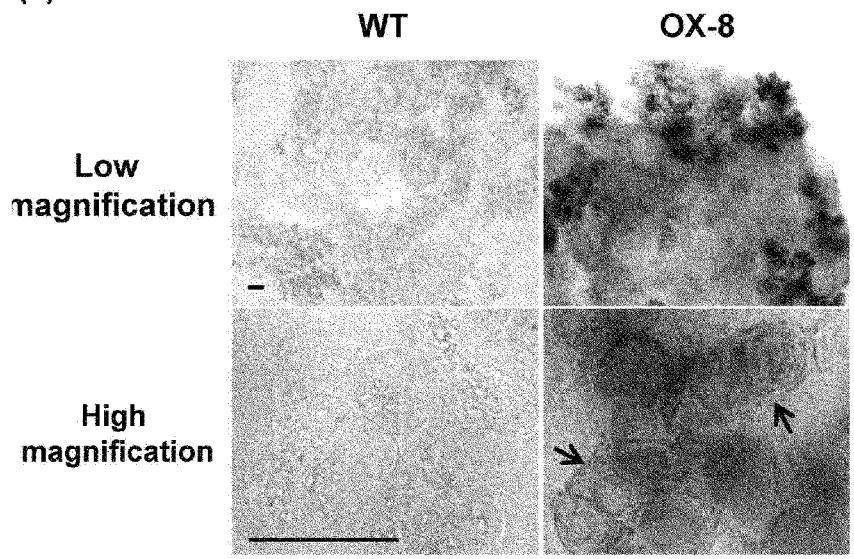
FIG. 7 shows images of lignifications of secondary cell walls and autophagic induction in RabG3bCA-cultured cell lines [(a) WT and OX-8-cultured cells stained with phloroglucinol-HCl, showing lignified xylem cells using an optical microscope; arrows indicate secondary cell wall patterns of vessel elements; (b) WT and OX-8-cultured cells stained with LTG, showing autophagic structures using a fluorescence microscope (left and middle images) and an optical microscope (right image); and Bars=100 µm].
Figure 7:
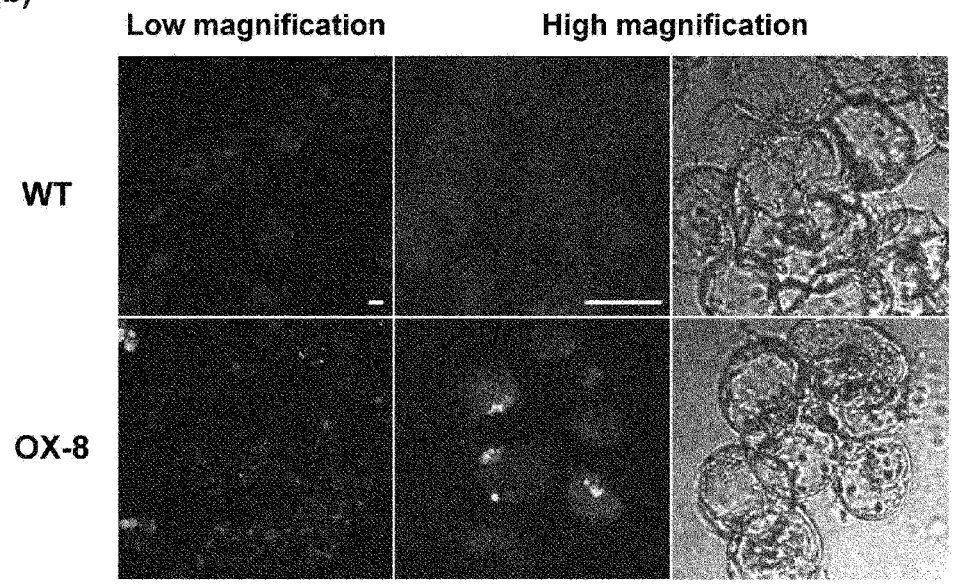

Previously, tracheary element-enhancing activity of RabG3b of *Arabidopsis thaliana* in a cell culture system and fluorescent stems allowed to define the role of autophagy in tracheary element differentiation [Kwon et al. (2010) *Plant Journal* 64, 151-164; Kwon et al. (2010) *Autophagy* 6, 1187-1189.]. The present inventors demonstrated that autophagy is an important process in the xylem differentiation, and proved as a factor involved in programmed cell death of the tracheary element of *Arabidopsis thaliana*. In a poplar, an autophagic structure was detected in differentiating xylem cells, and higher accumulation was observed in RabG3bCA transgenic trees from analysis of cut samples [FIG. 8]. Notably, in callus culture, while xylem differentiation or lignin deposition is not induced in the wild-type cell lines, xylem differentiation is increased and accompanies with the increase in formation of autophagic structures shown by acid staining in RabG3bCA transgenic cell lines [FIG. 7]. In the previous study, it was indicated that ATG genes and protein expression in *Arabidopsis thaliana* are related to autophagic activation in the tracheary element differentiation [Kwon et al. (2010) *Plant Journal* 64, 151-164; Kwon et al. (2010) *Autophagy* 6, 1187-1189]. According to the present invention, in growing poplar stems, several ATG genes were expressed two or more times higher than the wild-type cell lines in RabG3bCA-increased cell lines [FIG. 9(c)]. These results show that autophagy is an essential process of the xylem differentiation and regulated by GTPase activity of RabG3b in poplars like in *Arabidopsis thaliana*. Particularly, these results have industrial values because it is very rare that genetic characters of herbaceous plants such as *Arabidopsis thaliana* are exhibited in trees such as a poplar.

Programmed cell death is an important step in the tracheary element development, and occurs at the last stage. Previous studies have suggested that programmed cell death of tracheary elements is involved with autophagy during xylem differentiation [Fukuda H. (2000) *Plant Molecular Biology* 44, 245-253; Weir et al. (2005) *Cytometry Part A* 68A, 81-91.]. In addition, it is demonstrated that, in the tracheary element differentiation, autophagy is involved with programmed cell death caused by vacuole explosion [Kwon et al. (2010) *Plant Journal* 64, 151-164; Kwon et al. (2010) *Autophagy* 6, 1187-1189]. Gene expression, and histological and structural analyses of poplars show that RabG3b and autophagy are coupled with programmed cell death during the xylem development. In addition, it is noted that the accumulation of autophagic structures, vacuole collapse, and degradation of cell contents are largely enhanced in RabG3bCA transgenic poplars [FIG. 8]. Programmed cell death-related genes (i.e., MC9, peroxidase, and β-VPE) and ATG genes are highly expressed in the RabG3bCA transgenic poplars during xylem formation [FIG. 8(b)]. These results show that, like in *Arabidopsis thaliana*, RabG3b-mediated autophagy leads to programmed cell death, and the programmed cell death caused by autophagy is necessary for programmed cell death during the xylem differentiation in poplars.

In *Arabidopsis thaliana*, programmed cell death and autophagy appeared to be closely related with formation of secondary cell walls during tracheary element formation [Kwon et al. (2010) *Plant Journal* 64, 151-164]. Autophagic activation is accompanied by programmed cell death and secondary cell wall deposition in the RabG3bCA-increased cells. In contrast, none of tracheary element-related morphological changes are observed in autophagy-deficient RabG3bDN, RabG3bRNAi, atg5-1 cells. Programmed cell death and secondary cell wall-related genes are highly increased in tracheary element differentiation of the RabG3bCA-increased cells. Overexpression of RabG3bCA in poplars also leads to an increase in the expression of programmed cell death- and autophagy-related genes, and biosynthetic genes for secondary cell wall components [FIG. 9], suggesting the possibility of co-relation between the formation of a secondary cell wall and the programmed cell death in the xylem development.

Cellulose is the critical component for a secondary cell wall used in production of biofuel, and is degraded by a cellulase to a saccharide, thereby being converted into glucose [Abramson et al. (2010) *Plant Science* 178, 61-72]. Lignin and hemicelluloses act as physical barriers against the enzymatic digestion of cellulose, and therefore, genetic engineers and chemists have developed a method of reducing biosynthesis and increasing breakdown of lignin and xylan [Pilate et al. (2002) *Nature Biotechnology* 20, 607-612; Yang et al. (2004) *Biotechnology & Bioengineering* 86, 88-95; Weng et al. (2008) *Current Opinion in Biotechnology* 19, 166-172]. The results indicate that cell wall components of RabG3bCA transgenic stems were changed to improve the quality of trees used as a biofuel. (10% increases in cellulose and glucose, 25% decrease in xylan, but no significant change in lignin (Table 3)). The increase in the ratio of xylan to cellulose makes degradation of the secondary cell wall easier, and thus bioethanol production can be more improved [Sticklen M. (2006) *Current Opinion in Biotechnology* 17, 315-319; Pauly et al. (2010) *Current Opinion in Plant Biology* 13, 305-312].

Figure 5:
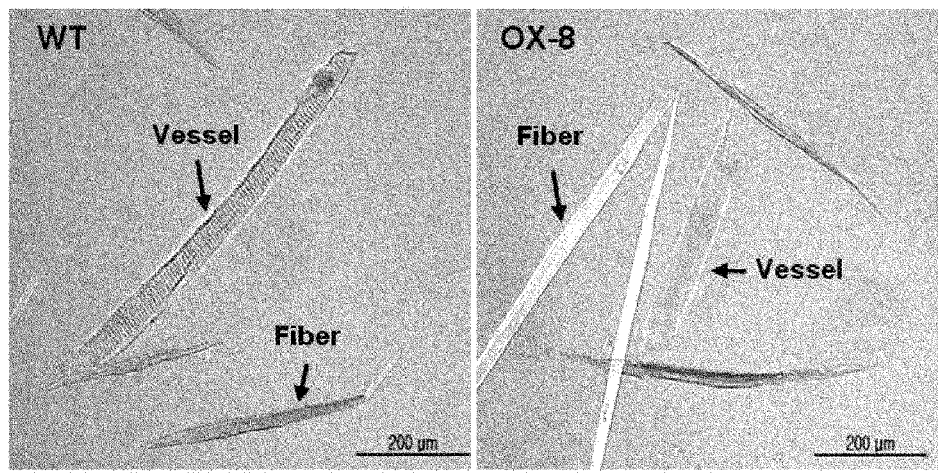
FIG. 5 shows changes in vessel elements and fiber cells of stems of the wild-type tree (WT) and the RabG3bCA transgenic poplar (OX).
Figure 6:
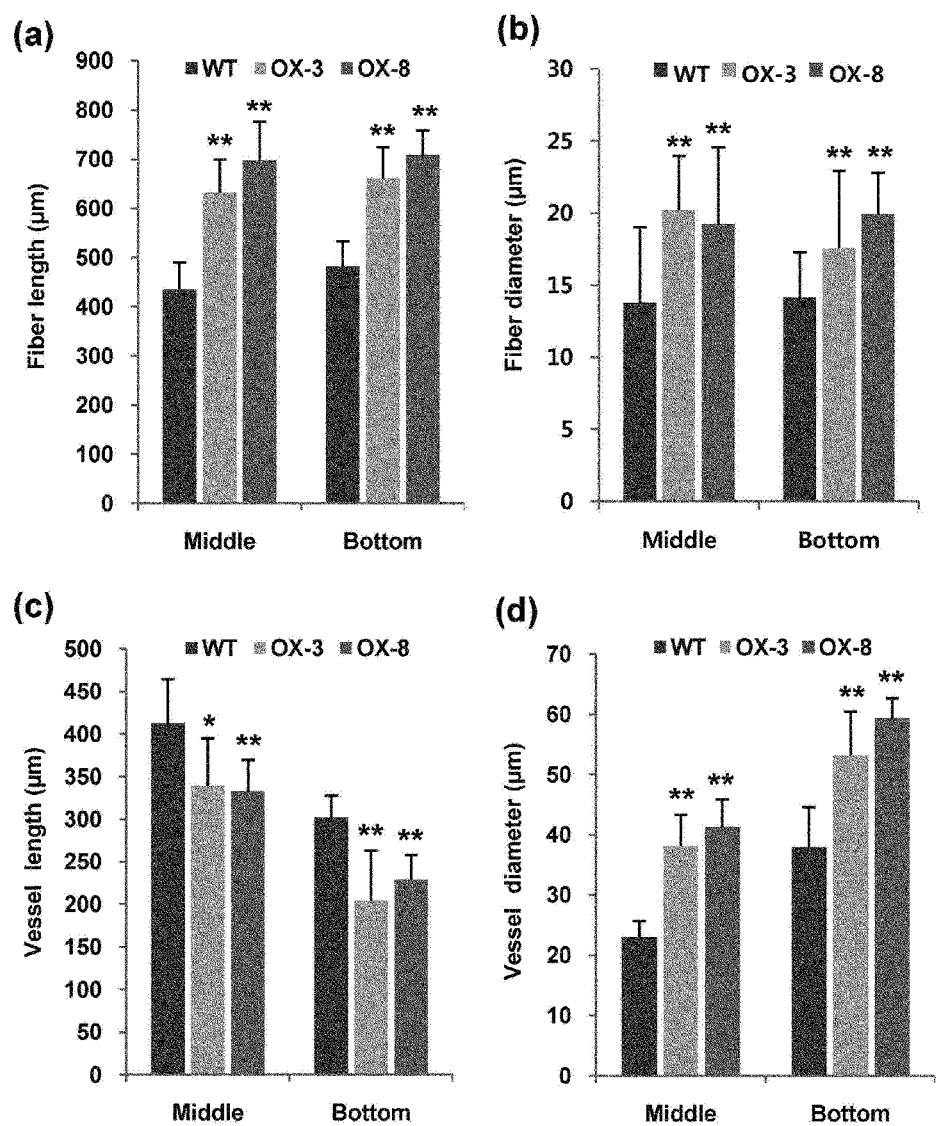
FIG. 6 shows changes in an xylem cell size of RabG3bCA transgenic trees (OX) [(a) fiber cell length; (b) fiber cell diameter; (c) vessel element length; (d) vessel element diameter; cells were obtained from bottom and middle parts of stems of 10-week-old WT and OX-8, and images were obtained by separating the xylem cells, means±standard deviation of 25 cells for each measurement; t-test; and *P<0.05 **P<0.01].

Interestingly, it is discovered that, in RabG3bCA transgenic poplar stems, fiber cells are 37 to 60% longer than those of wild-type poplar stems [FIGS. 5 and 6]. At initial stage of development, fiber cells are enormously elongated towards an axis, and thus a secondary cell wall becomes rigid, and programmed cell death occurs [Dejardin et al. (2010) *Comptes Rendus Biologies* 333, 325-334.]. The elongation of the fiber cells is similar to the growth of pollen tube and root hair, which leads to active transport of secretory vesicles towards a tip of the fiber cell through actin filaments [Chaffey et al. (2002) *Tree Physiology* 22, 239-249]. Direct transport of vesicles to the tip of the cell is very important for nutrient supply to the elongated zone, and this process of nutrient redistribution may be regulated by autophagy. In the process of making a paper, the length of the fiber cell is a very important factor, and thus the RabG3bCA transgenic tree can be used as a raw material to produce a paper or pulp.

In the case of RabG3bCA transgenic poplars, 20% or more of glucose is extracted from 100 g of a biomass even with a similar amount of lignin, compared to the wild-type tree. Such a result may be caused by an effect of the RabG3bCA gene leading to a faster growth particularly in OX8, a loose connection between cellulose and other wood components such as hemicelluloses and lignin, and easier approach of a cellulase towards cellulose due to less steric hindrance. In addition, considering a total weight of the biomass, OX8 is increased in weight twice or higher in the same period [refer to FIGS. 2 (e) and (f)], and thus glucose production is considerably enhanced.

In addition, after pre-treatment of a catalyst, the glucose yield varies depending on a catalyst. Though a hemicellulose removal rate in sulfuric acid is higher than when other catalysts are used, digestibility is in the lowest level. This is because approachability of an enzyme to a cellulose molecule is reduced due to a low recovery rate of cellulose and a low lignin removal rate. It is proved that sodium hydroxide is the most effective catalyst for poplars in terms of the sodium hydroxide digestibility and glucose yield.

The present inventors demonstrate that RabG3bCA overexpression leads to morphological changes in xylem development in both the herbaceous annual plant, which is *Arabidopsis thaliana*, and the perennial tree, which is a poplar. In addition, they also demonstrate that there is a physiological action leading to programmed cell death by RabG3b autophagy, and stimulating production of secondary cell walls during the formation of the tree. Based on the present invention, consistent increase in RabG3b and autophagic components can enhance tree quality, and can be applied to the forest industry. Moreover, factors known to have a relationship with RabG3b contribute to providing new data to a complicated network of the factors used in the xylem development and increasing physiological understanding of the tree.

Hereinafter, the present invention will be described in further detail with respect to Examples, but the scope of the present invention is not limited to the following Examples.

Examples

I. Materials and Test Method

1. Plants and Growth Condition

For poplar transformation, a hybrid poplar clone BH1 (*P. alba×P. tremula* var. *glandulosa* BH1) maintained on shoot tip culture was used. An RabG3bCA construct was cloned into a pBI121 plant expression vector previously [Kwon et al (2009) *Journal of Plant Biology* 52, 79-87.], and transferred to poplar cells via *Agrobacterium*-mediated transformation method [Choi et al (2005) *Journal of Plant Biology* 48, 351-355; Kim Y. H., Kim et al (2011) *Plant Biotechnology Journal* 9, 334-347]. The transformed cells were selected on a callus induction medium (Murashige and Skoog [MS] medium, pH 5.8, 3% sucrose, 0.8% agar, 1 mg/l 2,4-dichlorophenoxyacetic acid, 0.01 mg/l benzylaminopurine, and 0.1 mg/l 1-naphthylacetic acid [NAA]) containing 500 mg/L Cefotaxime and 50 mg/L kanamycin. Roots were transferred on a tree medium and regenerated. During the transformation, the medium may be maintained at 25° C. in a culture room, applied with white light (30 µmol/m$^2$·s) for 16 hours, and left for 8 hours under a dark condition. The regenerated roots were transferred to an MS medium containing 0.2 mg/l indolebutyric acid for rooting. The rooted plants were acclimatized in pots, and then transferred to soil in a greenhouse for further experiments. The plants were grown in the greenhouse at 28 to 30° C. for 12 hours under a light condition and 12 hours under a dark condition to carry out culture and experiments.

2. Measurement of Plant Growth

Plant growth was determined by measuring stem a length from a root apex to a stem base, a diameter at the stem base, and an internode number and length. As a control for initial plant lengths, plants grown 20 cm long in soil were cut at the base at the same time to start with the same initial length for measurements. The measurements were repeated three to five times.

3. Histochemical Analyses

Histochemical analyses were performed, as described previously [Kwon et al. (2010) *Plant Journal* 64, 151-164].

Poplar stems were fixed in a solution containing 2.5% glutaric aldehyde and 4% p-formaldehyde in a 0.1 M phosphate buffer (pH 7.4) for 4 hours at 4° C., rinsed in 0.1 M phosphate buffer (pH 7.4), and further fixed in 1% $OsO_4$ for 2 hours at room temperature. After samples were rinsed in 0.1 M phosphate buffer, the samples were dehydrated and embedded in an LR white resin (London Resin). Cross-sections (1 µm) were prepared using an ultramicrotome (RMC MT X), stained and photographed using a light microscope. The cross-sections were cut to a size of 60 to 70 nm, and briefly stained with filtered 1% toluidine blue. The cross-sections were photographed using a light microscope (Olympus, BX51TRF). According to a transmission electron microscopy (TEM) analysis, thin cross-sections (60 to 70 nm) were collected on copper grids (1-GN, 150 mesh), stained with uranyl acetate and lead citrate, and examined by TEM (Philips, Tecnai 12). For lignin autofluorescence analysis, poplar stems were fixed and embedded in paraplast (McCormick Scientific). Cross-sections (10 µm) were prepared using a microtome (Leica RM2235) and photographed using a confocal microscope (Zeiss LSM 510 META) at 405/460 nm excitation/emission. For lignin staining, cultured cells were stained with a phloroglucinol solution (2% ethanol/water, 95/5[v/v]) for 1 hour and soaked in 6 N HCl. Bright-field photographs of stained cell culture samples were taken using a light microscope (Olympus, BX51TRF).

For LysoTracker Green (LTG) staining, cultured cells were incubated with 1 µM LTG DND-26 (Molecular Probes) in the dark for 1 hour. Images were taken using a confocal microscope (Zeiss LSM 510 META) at 488/505 nm excitation/emission. Cultured cells for staining were prepared by incubating leaf discs on a callus induction medium for 5 weeks.

4. Preparation of Macerated Xylem Cells

To measure the size of vessel elements and fibers, stem parts (1 cm) taken from the bottom and middle parts of a wild-type tree and transgenic poplars grown in soil for 10 weeks were cut into pieces having a size of 2 mm×1 mm×2 mm. Tree pieces were immediately soaked in Schulze's reagent containing 6% $KClO_3$ in 50% nitric acid, and stored for up to 1 week at room temperature. The samples were then vigorously shaken for 30 minutes at 60° C. to separate the samples into individual cells. The macerated individual cells were washed with distilled water three times and mounted on microscope slides with cover glasses. Photographs were taken using an optical microscope (Olympus, BX51TRF) and used to measure the cell length and width.

5. Analysis of Secondary Cell Wall Components

Stem samples of plants grown in soil for 10 weeks were used to analyze cell wall components. Unnecessary components were extracted using acetone and hot water to remove.

Stems (2 g) were ground in liquid nitrogen to 40-60 mesh, extracted in 20 ml of acetone (99.9%, reagent grade) for 8 hours at room temperature, and filtered through a Whatman No. 2 filter paper. Acetone-extracted samples were then extracted in boiling water for 2 hours, filtered through a Whatman No. 2 filter paper, and allowed to air-dry.

The samples (200 mg) from which the unnecessary components were removed were dissolved in 72% sulfuric acid (1.5 ml) for 2 hours at 20° C. The resulting solution was diluted with boiling water containing 3% sulfuric acid, and the sample solution was boiled for 3 hours. The boiled sample solution was cooled to room temperature overnight to precipitate Klason lignin, and filtered through a 1G4 porcelain crucible filter.

A Klason lignin content (TAPPI Standard 222 om-88) of the filtered residue was analyzed. For analysis of monosaccharides, the experiment was performed at $\frac{1}{10}$ scale-down, and $2^{nd}$ stage hydrolysis accompanies dilution by deuterium oxide ($D_2O$) as an NMRsolution, instead of boiling water for $^1$H-NMR spectroscopic analysis [Shin et al (2008) *Cellulose* 15, 255-260].

Specific NMR conditions are as follows:

Broad band Observe Probe type, 30° C., 90°, 11 psec pulse, 10 sec delay between pulses, 2.73 sec for acquisition time, 10 ppm for sweep width.

A monosaccharide composition in cell walls was calculated based on the interpretation of the $^1$H-NMR spectra at the anomeric hydrogen peaks integral as described above [Shin et al (2008) *Cellulose* 15, 255-260].

6. Analysis of Cellulose Crystallinity

Cellulose crystallinity of the previously-prepared samples from which unnecessary components were removed was measured using an X-ray diffractometer (Bruker D5005) operated at 40 Kv and 40 mA.

The diffraction spectra were taken using the θ-2θ method, and duplicated samples were scanned at 1°/min from 2θ=10°-30° by 0.01°. The relative crystalline index was measured as described in the previous literature [Segal et al (1959) *Textile Research Journal* 29, 786-794].

7. Gene Expression Analysis

Total RNAs were isolated from poplar leaves to check for the expression of RabG3bCA in RabG3bCA overexpressing lines or from young stems to check for the expression of various genes by quantitative real time polymerization chain reaction (RT-PCR) using a plant RNA purification reagent (Invitrogen). The isolated samples were analyzed by quantitative RT-PCR.

Afterward, an RNase-free DNase I was treated to remove genomic DNA. For quantitative expression analysis, total RNAs (1.5 μg) were used for the synthesis of first-strand cDNAs using a power cDNA synthesis kit (iNtRON) according to a manufacturer's protocol.

The quantitative RT-PCR was performed using a KAPA SYBR FAST qPCR master mix in a Light Cycler 480 system (Roche).

Genes and specific primers were used, and corresponding gene model names are listed.

TABLE 1

Primers used in RT-qPCR

| Gene | Accession number | Forward primer | Reverse primer |
|---|---|---|---|
| For RT-PCR | | | |
| RabG3b | At1g22740 | ATGACAGGCTTGTCACATTGCA (SEQ ID NO: 2) | AGCACAACCTCCTCTTTGCTCA (SEQ ID NO: 3) |
| Actin | | CATTGGTGCTGAGCGATTCCGTTGC (SEQ ID NO: 4) | TTTTCATGCTGCTTGGGGCTAGTGC (SEQ ID NO: 5) |
| For real-time qRT-PCR | | | |
| 1) Monolignol synthesis-related genes | | | |
| 4CL3 | | ACTAGCCCATCCAGAGATATCCGA (SEQ ID NO: 6) | TCATCTTCGGTGGCCTGAGACTTT (SEQ ID NO: 7) |
| C3H3 | | GTATGACCTTAGTGAAGACACAAT-CAT (SEQ ID NO: 8) | CCCTTGGGTTCTTGATTAGCCTC (SEQ ID NO: 9) |
| CCoAOMT | | CAGTAATTCAGAAAGCTGGTGTTGC (SEQ ID NO: 10) | GCATCCACAAAGATGAAATCAAAAC (SEQ ID NO: 11) |
| COMT2 | | TCTTGAAGAATTGCTATGACGCCT (SEQ ID NO: 12) | GAATGCACTCAACAAGTATCACCTTG (SEQ ID NO: 13) |
| CAD1 | | GGCAAGCTGATCTTGATGGGTGTT (SEQ ID NO: 14) | TCCCGGTGATTGACnTCTCCCAA (SEQ ID NO: 15) |
| CAD4 | | TGACCGTCTGTCTTTGCTTTTAAA (SEQ ID NO: 16) | GGGACAGATCACCAGATGCA (SEQ ID NO: 17) |
| CAD10 | | TCCCATGTTCTCGAACCCTTTA (SEQ ID NO: 18) | CCAGGGTATTGCCGATGTTAAG (SEQ ID NO: 19) |
| 2) Carbohydrate synthesis-related genes | | | |
| CesA4 | | GAGTTAAGGAAGATGGAGAGGTGT (SEQ ID NO: 20) | TGCACTGAGGACAGGACTGGTTGC (SEQ ID NO: 21) |
| CesA7 | | TCGCCTTTCTCTCAGATACGAACG (SEQ ID NO: 22) | TTACCCGTAACAAGAGGGGGTTCC (SEQ ID NO: 23) |
| CesA8 | | GTTGGCCTCTGTCTTCTCTCTTGTC (SEQ ID NO: 24) | CAATCTATAGAAATGCAGGTTTCAC (SEQ ID NO: 25) |
| CesA18 | | GTTGGCCTCTGTCTTCTCTCTTGTT (SEQ ID NO: 26) | CAATCAATGGAAATGCAGGTCTCCG (SEQ ID NO: 27) |
| IRX8 | | GAAAATTTCAAGCCCAACGA (SEQ ID NO: 28) | CTGGAGGCAGTGTTCCTAGC (SEQ ID NO: 29) |
| IRX9 | | GGCTGAGTGGGATTGTTCAT (SEQ ID NO: 30) | AGGCCTTTTATCCGTTTCGT (SEQ ID NO: 31) |
| FRA8 | | ACGTTTGACCCATACGAAGC (SEQ ID NO: 32) | CGTGAGAGGCAACAAAGACA (SEQ ID NO: 33) |

TABLE 1-continued

Primers used in RT-qPCR

| Gene | Accession number | Forward primer | Reverse primer |
|---|---|---|---|
| 3) PCD-related genes | | | |
| MC9 | | GCTAGCCATGAAGGAAGTGC (SEQ ID NO: 34) | GGAATCCATGTTCCATGTCC (SEQ ID NO: 35) |
| Peroxidase | | TTTGCTGAGGCAATTGTGAG (SEQ ID NO: 36) | GCCTCTCACGCTTTGATTTC (SEQ ID NO: 37) |
| β-VPE | | TCGCAGTATGGGATGAAACA (SEQ ID NO: 38) | GCTTCAATTAGGCGCTGAAC (SEQ ID NO: 39) |
| 4) Autophagy-related genes | | | |
| ATG8d1 | | CAGCCACGAGTTCTTCATCA (SEQ ID NO: 40) | AGACAAACTGCCCCACAGTC (SEQ ID NO: 41) |
| ATG8f2 | | ACTCCAAACGTCTCCCCTTT (SEQ ID NO: 42) | CATGCTCTTGCTTGAAGCTG (SEQ ID NO: 43) |
| ATG8i | | AGCAAAGGCTGGAAGAATCA (SEQ ID NO: 44) | TGAATGAATTGCCCAACAGA (SEQ ID NO: 45) |
| 5) Reference Genes | | | |

TABLE 2

Genes associated between poplars and *Arabidopsis thaliana*

| Gene | Gene model name |
|---|---|
| 1) Monolignol synthesis-related genes | |
| 4CL3 | grail3.0004045401 |
| C3H3 | estExt_fgenesh4_pm.C_LG_VI0096 |
| CCoAOMT1 | grail3.0001059501 |
| COMT2 | estExt_fgenesh4_pm.C_LG_XII0129 |
| CAD1 | estExt_Genewise1_v1.C_LG_IX2359 |
| CAD4 | eugene3.20690001 |
| CAD10 | estExt_fgenesh4_pg.C_LG_12533 |
| 2) Carbohydrate synthesis-related genes | |
| CesA4 | eugene3.00002636 |
| CesA7 | estExt_Genewise1_v1.C_LG_VI2188 |
| CesA8 | Gw1.XI.3218.1 |
| CesA18 | eugene3.00040363 |
| IRX8 | estExt_fgenesh4_pm.C_LG_XIII0357 |
| IRX9 | estExt_Genewise1_v1.C_LG_XVI2679 |
| FRA8 | grail3.0001137701 |
| 3) PCD-related genes | |
| MC9 | grail3.0101007801 |
| Peroxidase | fgenesh4_pg.C_LG_XIX00050 |
| β-VPE | grail3.0013022501 |
| 4) Autophagy-related genes | |
| ATG8d1 | estExt_Genewise1_v1.C_LG_XIV3313 |
| ATG8f2 | eugene3.00021333 |
| ATG8i | estExt_fgenesh4_pg.C_LG_III1864 |
| 5) Reference genes | |
| EF1a | Grail3.0028013201 |
| 18S | Tuskan et al. (2006) |

The tested gene expression levels were standardized to the constitutive expression level of 18S rRNA, and calculated using the $2^{-\Delta\Delta}$ method [Schmittgen et al. (2008) *Nature Protocols* 3, 1101-1108].

The experiments were repeated three times with biologically independent samples.

8. Western Blotting

Weston blotting was performed as described, previously [Kwon et al. (2009) *Journal of Plant Biology* 52, 79-87.].

Proteins were separated on a 15% SDS-polyacrylamide gel, transferred onto a nitrocellulose membrane, and then incubated with an anti-RabG3b antibody overnight at 4° C.

The antibody-binding proteins were incubated with conjugated secondary antibodies and detected using an ECL system (Amersham Biosciences).

9. Southern Blot Analysis

Genomic DNA was extracted from poplar leaves using a DNAzol solution (MRC) [Chomczynski et al. (1997) *BioTechniques* 22, 550-553.], and digested overnight with the restriction enzyme EcoRI.

Afterward, the digested DNA was separated on a 0.7% agarose gel, and transferred onto a Hybond-XL membrane (Amersham Bioscience).

The blot was hybridized with a [$\alpha$-$^{32}$P]dCTP-labeled RabG3b cDNA probe in a hybridization buffer for 24 hours at 60° C.

The hybridized blot was washed continuously with 2×SSC and 1×SSC for 30 minutes at 50° C., and then exposed to an X-ray film.

10. Pre-Treatment

In the experiments, for pre-treatment of poplars, three kinds of catalysts containing sulfuric acid (Daejung Chemicals & Metals, Gyeonggi, Korea), sodium hydroxide (Sigma-Aldrich, St. Louis, Mo.) and aqueous ammonia (Junsei, Tokyo, Japan) were used. For ammonia treatment, grinded poplars were incubated in a 14% (w/w) aqueous ammonia solution contained in a water bath (Biofree, Seoul, Korea) for 10 hours at 80° C. When the sulfuric acid and sodium hydroxide were treated, the temperature was increased to 190° C. within 3 minutes, and the poplars were soaked in each of the 1% (w/w) catalysts in a microwave oven. Subsequently, to inhibit the reaction, a microwave container was transferred into an ice water. After each treatment was ended, a pretreated biomass was filtrated through a filtration cloth (22-25 μm, Calbiochem, La Jolla, Calif.), washed with a sufficient amount of water to have a pH of the resulting liquid of 6 to 7, and dried in an oven for 3 days.

11. Enzymatic Hydrolysis

To examine pre-treatment efficiency, both the non-treated and pre-treated poplars were digested according to the NREL procedure [Selig, M., Weiss, N., Ji, Y. 2008. Laboratory analytical procedure: enzymatic saccharification 202 of lignocellulosic biomass. National Renewable Energy Laboratory, Golden, Colo.]. Enzyme activity was measured at 56.8 FPU per 1 ml solution. A 1% (w/v) biomass was added to 20 ml vial previously contained with a 0.05 M of citric acid buffer and antibiotics such as tetracycline and cycloheximide, and incubated using the Accellerase 1000 (Genencor, Rochester, N.Y.) at 15 FPU per 1 g of glucan for 72 hours. To check profiling of an enzyme-substrate reaction, samples were collected at 2, 6, 10, 24, 48, and 72 hours, respectively.

12. Componential Analysis

Componential analysis was performed according to the NREL procedure [Sluiter, A., Hames, B., Ruiz, R., Scarlata, C., Sluiter, J., Templeton, D., Crocker, D. 2008. 210 Laboratory analytical procedure: determination of structural carbohydrates and lignin 211 in biomass. National Renewable Energy Laboratory, Golden, Colo.]. In summary, 0.3 g of dry biomass was pre-digested using 72% (w/w) sulfuric acid, diluted to a concentration of 4%, and digested for 1 hour at 121° C. A biomass slurry was filtrated through a crucible. Residues on the crucible were transferred into a furnace for 3 hours at 575° C. (Daihan LabTech, Kyonggi-Do, Korea). Acid-insoluble lignin was determined by measuring a difference in weight before and after combustion in the furnace. Carbohydrates including glucose, xylose, etc. were analyzed using high performance liquid chromatography (HPLC; Agilent 1100, Agilent Technologies, Waldbronn, Germany) equipped with a SP0810 column (Shodex, Showa Denko, Kawasaki, Japan; $Pb^{2+}$ form, 300 mm×8.0 mm×7 μm) and a refractive index meter (G1362A, Agilent Technologies, Waldbronn, Germany) by centrifuging a flow-through for 5 minutes at 16,000 rpm, and filtering the resulting product through a 0.2 μm syringe filter (Chrom Tech, Apple Valley, Minn.). The analysis was repeated three times.

II. Results of Experiments

1. Construction of RabG3bCA Transgenic Poplar

According to in silico data, *Arabidopsis thaliana* RabG3b is highly expressed under conditions of xylem differentiation such as brassinolide/boric acid ($H_3BO_3$) treatment and programmed cell death [Kwon et al. (2009) *Journal of Plant Biology* 52, 79-87; Kwon et al. (2010) *Plant Journal* 64, 151-164.]. In the previous study, RabG3b was shown to regulate tracheary element differentiation through its role in autophagy in *Arabidopsis thaliana* [Kwon et al. (2010) *Plant Journal* 64, 151-164]. To investigate whether RabG3b performs similar functions in both poplar and *Arabidopsis thaliana*, and thus enhances xylem development in poplars, the present inventors generated RabG3bCA transgenic poplars by overexpressing a constitutively active form RabG3b from a cauliflower mosaic virus 35S promoter. Using RT-PCR and Western blotting, 14 lines were verified from transgene expression, which showed good correlation between transcription and protein levels [FIG. 1].

Nine lines (OX-1, -3, -7, -8, -11, -12, -13, -15, and -16) exhibited single copy insertions. Based on these results, three independent lines (OX-3, -8, and -15) showing high expression levels and single gene copy were selected for a further study.

2. Expressed Phenotypes of RabG3bCA Transgenic Poplars

Figure 2:
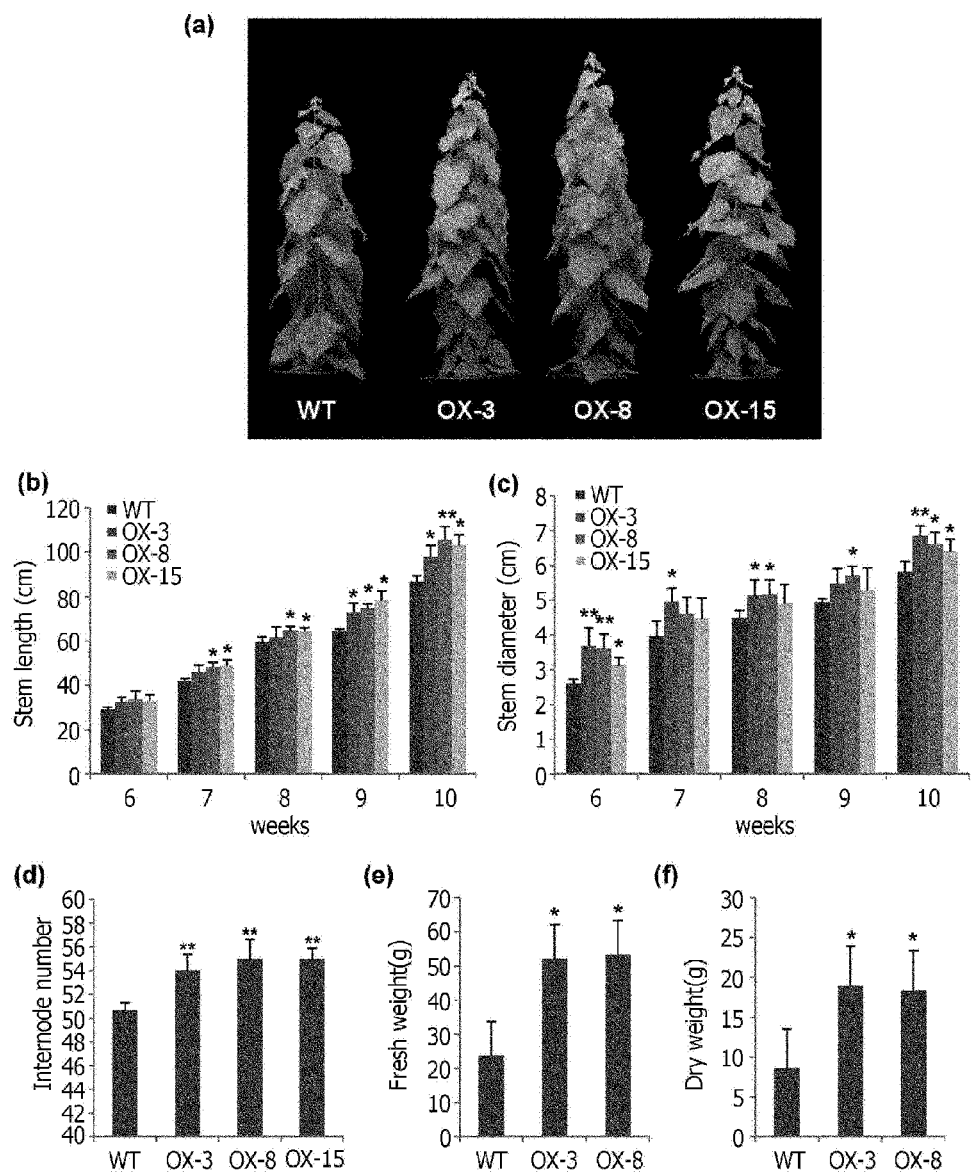
FIG. 2 shows the morphological comparison between the RabG3bCA transgenic poplar (OX) and the wild-type tree (WT) [(a) an image showing the comparison between the transgenic poplar (OX) and the wild-type tree (WT) after being grown in soil for 10 weeks; (b) length of a stem; (c) a diameter of a stem; growth of stems of the transgenic poplar (OX) and the wild-type tree (WT) was measured at 1 week intervals for 10 weeks (b and c); (d) the comparison of the number of annual rings between the transgenic poplar (OX) and the wild-type tree (WT) grown for 10 weeks; (e) the comparison of weight before drying between the transgenic poplar (OX) and the wild-type tree (WT) grown for 10 weeks; (f) the comparison of dry weight between the transgenic poplar (OX) and the wild-type tree (WT) grown for 10 weeks; a means±standard deviation was obtained by calculating standard deviation for 5 times, t-test; and *P<0.05 **P<0.01].

Stem growth of RabG3bCA transgenic poplars was examined [FIG. 2(*a*)]. The transgenic poplars (*P. alba*×*P. tremula* var. *glandulosa*; OX) in both the medium and soil were grown faster than a control (WT). In the culture medium, the control was grown 5 cm, and the transgenic trees were grown approximately 7 to 8 cm for 5 weeks. When measured 10 weeks after transfer to soil, stems of RabG3bCA transgenic trees were further grown 13 to 20% than the control in length and 10 to 12% in thickness, based on the control [FIGS. 2 (*b*) and (*c*)]. An internode number was also increased by approximately 10% in the transgenic poplars [FIG. 2(*d*)]. In addition, when a dry weight of the trees was measured, the RabG3bCA transgenic trees were weighed twice or more than the control [FIGS. 2(*e*) and (*f*)].

3. Xylem Development and Increase of Fiber Cells in RabG3bCA Transgenic Poplars

Increased stem growth caused by enhanced xylem development in RabG3bCA transgenic poplars, as in RabG3bCA transgenic *Arabidopsis thaliana*, was determined by anatomical analysis [Kwon et al. (2010) *Plant Journal* 64, 151-164].

Figure 3:
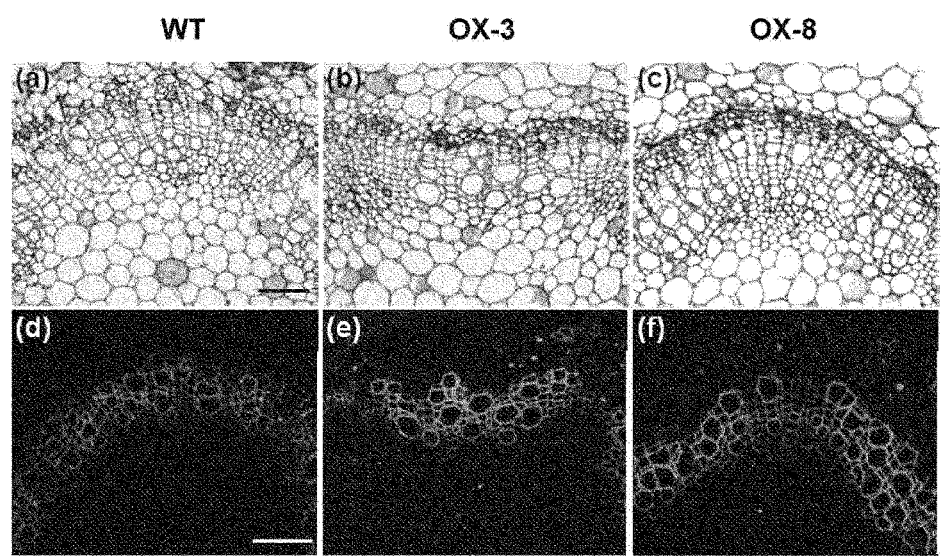
FIG. 3 shows changes in vascular development of RabG3bCA transgenic poplars [(a)-(c): cross-sections of the stem bases stained with toluidine blue, showing patterns of a vascular bundle; (d)-(f): cross-sections of the stem bases identified by lignin fluorescence, showing accumulation of lignin in xylem cells; resin-embedded cross-sections were prepared from the bottom parts of the wild-type trees (a and d) and the transgenic trees (b, c, e, and f), trees were grown in a culture medium for 5 weeks. Bars=50 µm].
Figure 4:
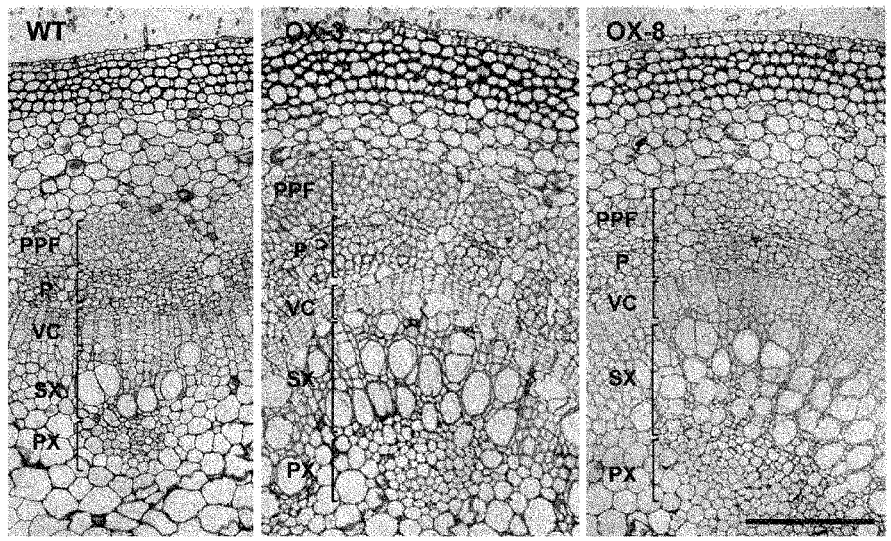
FIG. 4 shows xylem development enhanced in RabG3bCA transgenic trees [(a) cross-sections of stems from the 10$^{th}$ internode of the wild-type tree (WT) and the transgenic poplar (OX) stained with toluidine blue, showing distribution of the primary phloem fiber (PPF), phloem (P), vascular cambium (VC), secondary xylem (SX), primary xylem (PX); (b) cross-sections of stems from the 30$^{th}$ internode of the WT and OX stained with toluidine blue, showing distribution of the outer bark (OB), P, cambium (C), and xylem (X); Bars=200 µm (a and b); comparison of widths of tissues from the samples used in (c) and (b) (means±standard deviation); at 10 or more times measurements, t-test; and **P<0.01].
Figure 4:
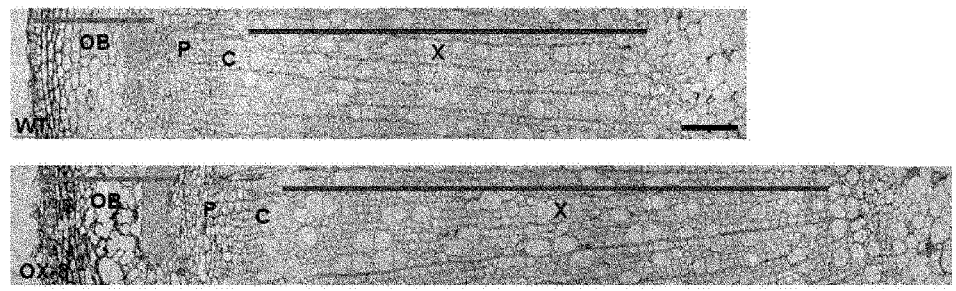
Figure 4:
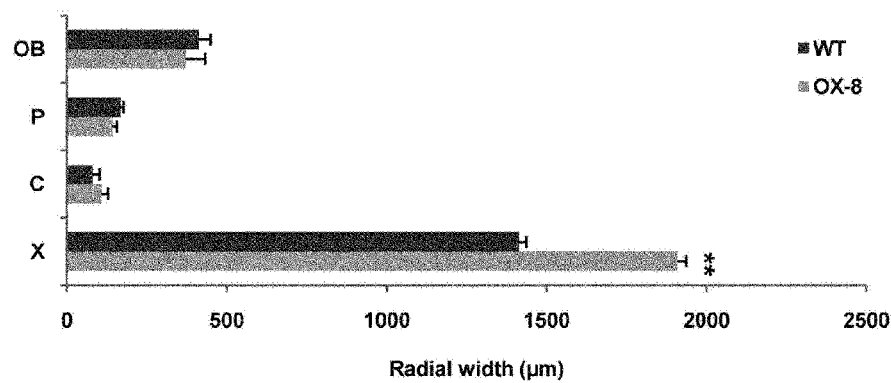

Trees grown in a medium for 5 weeks were cut at the bottom part of the stem to observe vascular bundle patterns [FIG. 3]. Although the overall vascular bundle shape of transgenic trees was similar to that of the control, a notable increase in xylem deformation was found in the transgenic trees [FIG. 3(*a*) to (*c*)]. Lignin fluorescence analyses revealed that lignifications and secondary cell wall formation were more enhanced in RabG3bCA transgenic trees than the control [FIG. 3(*d*) to (*f*)]. Vascular bundle development was further observed in trees grown in soil. In cross-sections at the $10^{th}$ internode of the upper part of a stem, a secondary xylem was apparently developed in transgenic trees, but was in the initial stage in the control [FIG. 4(*a*)]. Additional cross-sections were taken from the lower part of a stem undergoing secondary growth from the $30^{th}$ internode [FIGS. 4 (*b*) and (*c*)]. According to the observation of tissue parts, growth of the secondary xylem (SX) 40% wider than the control was shown in the transgenic trees. However, in the phloem (P), vascular cambium (C), and outer bark (OB), there was little difference between the transgenic trees and the control. These results demonstrate that overexpression of RabG3bCA in poplars enhances the growth of the secondary tree by enhancing xylem growth.

To determine an influence of xylem cell sizes on transgenic trees, vessels and fiber cells were separated, and the widths and lengths of the cells were measured [FIGS. 5 and 6].

In the RabG3bCA transgenic trees, the length of the fiber cell was significantly increased (45 to 60% and 37 to 47% increases in middle and bottom parts), the diameter of the fiber cell was also significantly increased (40 to 47% and 25 to 41% increases in middle and bottom parts), the vessel element diameter was also significantly increased (40 to 57% and 66 to 80% increases in middle and bottom parts), but the vessel element length was not significantly increased (18 to 20% and 24 to 33% decreases in middle and bottom parts).

4. Chemical Composition of Stem of RabG3bCA Transgenic Poplar

The cell wall components of a stem of the RabG3bCA transgenic poplar were analyzed for compositional changes [Table 3].

TABLE 3

Comparison in secondary cell wall components between wild-type cells and RabG3bCA transgenic cells

|  | WT | OX-3 | OX-8 |
|---|---|---|---|
| Klason lignin | 17.5 ± 2.3 | 19.5 ± 0.3 | 16.9 ± 1.1 |
| Polysaccharides | 82.5 | 80.5 | 83.1 |
| Cellulose | 51.8 ± 1.6 | 54.7 ± 1.3 | 57.2 ± 1.2 |
| Glucose | 52.9 ± 1.7 | 56.0 ± 1.3 | 58.6 ± 1.4 |
| Xylan | 28.1 ± 1.8 | 22.8 ± 0.6 | 22.3 ± 0.4 |
| Xylose | 28.1 ± 1.9 | 22.9 ± 0.6 | 22.4 ± 0.4 |

When two major structural components, cellulose and lignin, were measured, there was no change in lignin content in the transgenic poplars, compared to the control, but the cellulose content was increased approximately 10% (OX-8). The total saccharide content was similar in the control and the transgenic poplars. The amount of glucose, which was the primary component of the cellulose, was approximately 6 to 11% higher in the transgenic trees than in the control. Conversely, xylan (hemicellulose) and xylose (a main component of xylan) were significantly reduced by 23 to 26% in the transgenic trees. There was no difference in crystallinity of the cellulose between the control and the transgenic trees.

TABLE 4

Cellulose crystallinity

| Plant | Cellulose crystallinity (%) |
|---|---|
| WT | 70.5 ± 0.8 |
| OX-3 | 72.6 ± 0.7 |
| OX-8 | 72.2 ± 0.6 |

5. Activation of Autophagy During Xylem Development in Poplars

In the previous study, autophagy was activated in differentiating tracheary elements in *Arabidopsis thaliana*, and the differentiation of the autophagy and tracheary element was significantly stimulated by overexpression of RabG3bCA [Kwon et al. (2010) *Plant Journal* 64, 151-164]. Callus was increased from poplar leaves, and grown in a MS solid medium. Although a callus culture medium was not suitable for the xylem differentiation, the present inventors demonstrate that spontaneous xylem increase in RabG3bCA transgenic tree cells was induced by lignin staining with phloroglucinol-HCl [FIG. 7 (*a*)]. Approximately 20 to 30% stronger lignin staining was observed in the cell lines of the RabG3bCA transgenic trees, but was not observed in the control. Notably, some of stained cell lines of the RabG3bCA transgenic trees showed remarkable secondary cell wall patterns of vessel elements [FIG. 7(*a*), arrows]. This shows that lignin accumulation and xylem differentiation are increased in the cell lines of the RabG3bCA transgenic trees under a condition in which xylem differentiation is not stimulated in wild-type cells.

The possibility of the increase in autophagy was examined in cell lines of the RabG3bCA transgenic tree by staining autophagic structures with an acid dye such as LysoTracker Green (LTG) [Via et al. (1998) *Journal of Cell Science* 111, 897-905; Kwon et al. (2010) *Plant Journal* 64, 151-164][FIG. 7(*b*)]. A larger number of spots stained with the acid dye were detected in the cell lines of the RabG3bCA transgenic tree than those of the wild-type tree.

Figure 8:
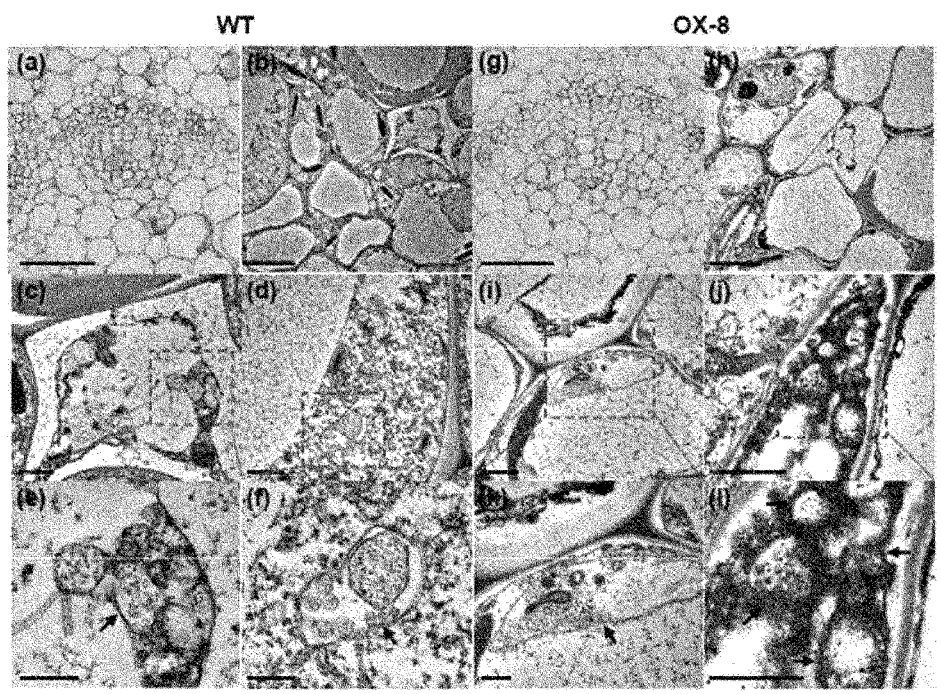
FIG. 8 shows formation of autophagic structures in differentiating poplar stems [(a,g) cross-sections of stems from the 2$^{nd}$ internode of WT (a) and OX-8 (g) stained with toluidine blue; (b and h) transmission electron microscopy (TEM) images with low magnification, showing differentiating xylem cells; (c, d, i, and j) TEM images of autophagic structures in differentiating xylem cells of WT (c and d) and OX-8 (i and j) stems; images (c, d, i, and j) in boxes were enlarged into (e, f, k, and l); arrows indicate autophagosome/autolysosome structures; and Bars=50 µm (a and g), 5 µm (b and h), 1 µm (c, d, i, and j), and 0.5 µm (e, f, k, and l)].

To examine whether the staining results were directly applied to poplars, samples obtained from the $2^{nd}$ internode were analyzed by a scanning electron microscope (SEM) [FIG. 8]. Differentiation of the primary xylem cell lines was observed in both the wild-type tree and transgenic tree [FIGS. 8(*a*) and (*g*)]. Wild-type xylem cells remained intact and were filled with cell contents, and in some cells, secondary cell walls were deposited [FIG. 8(*b*)], indicating that these cells were in the initial stage of the differentiation. Notably, in the wild-type cells, autophagic structures surrounded and degraded cell organelles and structures [FIG. 8(*c*) to (*f*)]. In contrast, xylem cells of the RabG3bCA transgenic tree largely underwent vacuole collapse and degradation of cell contents [FIG. 8(*h*)], and numerous autophagic structures were accumulated [FIG. 8(*i*) to (*l*)]. These results suggest that autophagy may occur in xylem differentiation, and the xylem differentiation and autophagy were more actively performed in RabG3bCA transgenic poplars.

6. Analysis of Xylem Development-Related Genes

Based on previous results for xylem development in *Arabidopsis thaliana* and poplars, various groups of genes involved in xylem development were selected, and their expression was analyzed in young stems of wild-type and RabG3bCA transgenic poplars while the xylem differentiation was progressing [Courtois-Moreau et al. (2009) *Plant Journal* 58, 260-274; Du et al. (2009) *Plant Journal* 60, 1000-1014; Shi et al. (2010) *Plant & Cell Physiology* 51, 144-163; Song et al. (2010) *New Phytologist* 187, 777-790].

Figure 9:
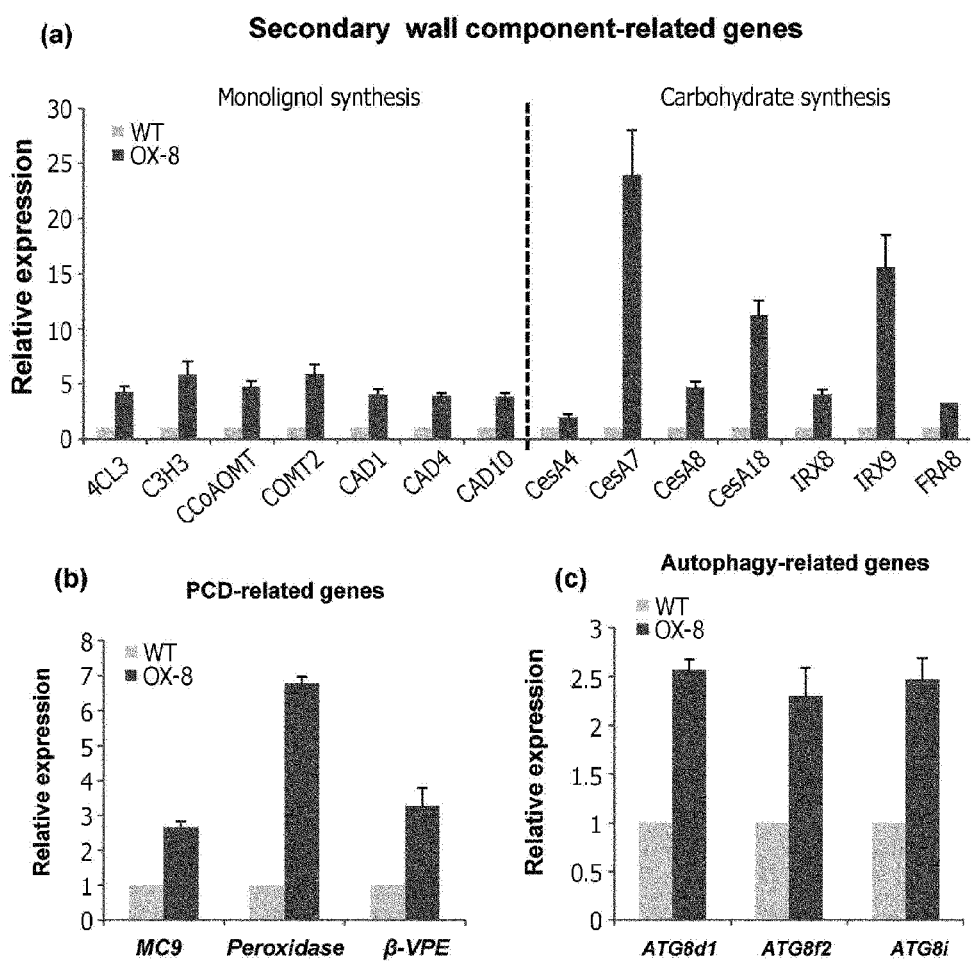
FIG. 9 shows expression analysis of xylem development-related genes in young poplar stems [(a) comparisons of genes related to formation of secondary cell walls; (b) comparison of genes involved with programmed cell death; (c) comparison of autophagy-related genes, results represent means±standard deviation at three measurements].

The present inventors compared expression of two groups associated with secondary cell wall formation (monolignol synthesis genes (4CL3, C3H3, CCoAOMT1, COMT2, CAD1, CAD4, and CAD10) and cell wall carbohydrate synthesis genes (CesA4, CesA7, CesA8, CesA18, IRX8, IRX9, and FRA8)) [FIG. 9(*a*)]. Most of the cell wall synthesis genes excluding a few genes (e.g. CesA4) were increased in the RabG3bCA transgenic tree. In addition, the present inventors analyzed the expression of two groups of genes specific to cell content degradation: expression of programmed cell death-related genes (peroxidase, VPE, and MC9) and autophagy-related genes (ATG8d1, ATG812, ATG8i) [Courtois-Moreau et al. (2009) *Plant Journal* 58, 260-274][FIGS. 9(*b*) and (*c*)]. Like phenotypic characteristics of the transgenic trees, that is, increase in degradation of cell walls and formation of an autophagic structure, these genes were increased in the transgenic trees. These results demonstrate that transgenic phenotype and xylem differentiation are associated with expression of these genes in the RabG3bCA transgenic trees.

7. Examination of Enzyme Accessibility

To indirectly examine enzyme accessibility to cellulose, three kinds of poplars including WT, OX3, and OX8 were hydrolyzed using Accellerase 1000 at 15 PFU per 1 g glucan for 72 hours. When the WT was hydrolyzed, based on the theoretically maximum glucose, 32.8% of digestibility was yielded. Such a relatively low digestibility may be caused by natural digestion resistance and rigidity of a lignocellulose. However, in a most non-treated biomass, a cellulose hydrolysis yield detected at usually less than 20% was slightly higher. In OX3 and OX8, the hydrolysis yields were obtained at 33.9% and 42.9%, respectively. Although OX3 did not show an optional difference, OX8 exhibited approximately 10% improvement of digestibility even with the lignin content similar to WT. Such a result proved that the RabG3bCA gene had an influence on phenotypic characters such as the length and thickness, and compositional characteristics or features without optional significant changes. Accordingly, for an increased biomass hydrolysis yield, various pre-treatment was applied to both conventional and transgenic poplars.

Sulfuric acid, sodium hydroxide, and ammonia were used as catalysts for pre-treating a lignocellulose. For each catalyst, pre-treatment conditions were determined based on the previous study. For WT, in sulfuric acid, sodium hydroxide, and ammonia pre-treatments, insoluble solid recovery rates using a 60 FPU cellulase were 49.0%, 58.7%, and 67.2%, respectively, and enzymatic digestibilities were 54.4%, 58.7%, and 44.9%, respectively. In each treatment, due to slight delignification of 23.8%, 37.3%, and 36.4%, compared to non-treated WT exhibiting digestibility of 34.8%, the digestibility was increased 1.6, 1.7, and 1.3 times, respectively. In the case of transgenic poplars including OX3 and OX8, overall results were somewhat similar to those in the WT. In the case of OX3, the insoluble solid recovery rates in the sulfuric acid, sodium hydroxide, and ammonia pre-treatments, were 43.5%, 58.2%, and 66.3%, respectively, and enzymatic digestibilities were 69.4%, 74.3%, and 53.3%, respectively. Under the pre-treatment conditions, a lignin content was decreased to 30.5%, 37.3%, and 34.1%, and for non-treated OX3, based on a digestibility of 35.1%, a lignin content was increased 2.0, 2.1, and 1.5 times. Finally, insoluble solid recovery rates of OX8 pre-treated with sulfuric acid, sodium hydroxide, and ammonia were 44.1%, 60.0%, and 63.7%, respectively, and enzymatic digestibilities thereof were 61.9%, 69.4%, and 61.3%, respectively. In addition, under each pre-treatment condition, when delignification was 27.6%, 37.6%, or 38.4%, compared to the digestibility of the treated OX8 of 43.0%, the digestibility was improved 1.4, 1.6, or 1.4 times. According to the experiment for ammonia recycled percolation hybrid poplars, although 60% or more of lignin was removed, digestibility using 15 FPU of a cellulase was 50% or less due to remaining lignin and non-productive binding of an enzyme with lignin. Thus, in the present study, the transgenic poplars, OX3 and OX8, may be lignocelluloses suitable to produce a high value-added product such as ethanol.

Figure 10:
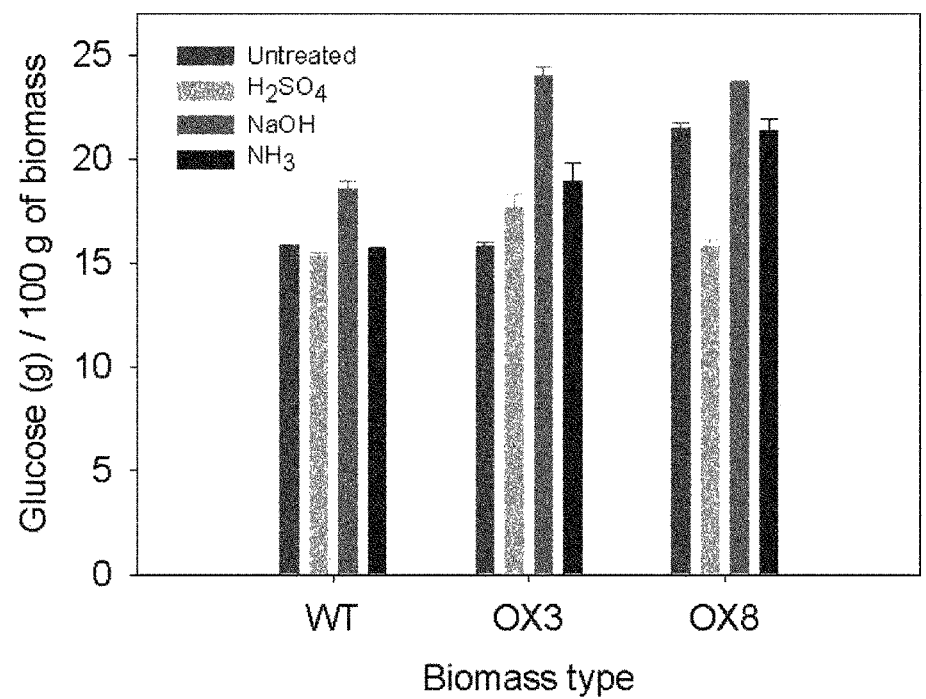
FIG. 10 shows glucose yields of three poplars (WT, OX-3, and OX-8) before and after each independently treated with sulfuric acid, sodium hydroxide, and aqueous ammonia catalysts.

From these results, as shown in FIG. 10, to evaluate efficiencies of catalysts for pre-treating conventional and genetically-manipulated poplars, a total glucose yield (insoluble solid×glucan content×enzymatic digestibility) obtained by enzymatic saccharification was compared. In the cases of non-treated WT, OX3, and OX8, based on a dry weight of 100 g, yields of the produced glucose were 15.9, 15.8, and 21.5 g, respectively. From 100 g of pre-treated poplars, the glucose yields were calculated within 15.3 to 18.5 g for WT, within 17.7 to 24.0 g for OX3, and within 15.8 to 23.7 g for OX8.

SEQ. ID. NO: 1: *Arabidopsis* RabG3b Constitutively Active Gene

While the invention has been shown and described with reference to certain exemplary embodiments thereof, it will be understood by those skilled in the art that various modifications in form and details may be made therein without departing from the spirit and scope of the invention as defined by the appended claims.

The invention claimed is:

1. A transgenic poplar tree comprising RabG3bCA gene that is a RabG3b constitutively active mutant, wherein the fiber cell length of said transgenic poplar tree is increased compared to that of a wild-type poplar tree; and the amount of xylem tissue is increased in said transgenic poplar tree compared to that of a wild-type poplar tree.

2. The transgenic poplar tree according to claim 1, wherein the RabG3bCA gene comprises a base sequence of SEQ. ID. NO: 1.

3. The transgenic poplar tree according to claim 1, wherein the RabG3b is derived from *Arabidopsis thaliana*.

4. The transgenic poplar tree according to claim 1, wherein a cellulose and/or glucose content is increased, compared to a corresponding wild-type poplar tree.

5. A method of producing biomass using a tree, wherein the tree is the transgenic tree of claim 1.

6. The method according to claim 5, wherein the tree is pre-treated with sodium hydroxide, and hydrolyzed with an enzyme to produce a biomass.

7. A method of producing a pulp using a tree, wherein the tree is the transgenic tree of claim 1.

* * * * *